United States Patent [19]

Lerner et al.

[11] 4,052,428

[45] Oct. 4, 1977

[54] STABLE ALUMINUM ALKOXIDE SOLUTIONS

[75] Inventors: Robert Wendell Lerner, Trumbull, Conn.; Russell S. Towers; John Robert Flasch, both of Adrian, Mich.

[73] Assignee: Stauffer Chemical Company, Adrian, Mich.

[21] Appl. No.: 640,502

[22] Filed: Dec. 15, 1975

[51] Int. Cl.$^2$ .................................................. C07F 5/06
[52] U.S. Cl. ............................................ 260/448 AD
[58] Field of Search ................................... 260/448 AD

[56] References Cited

U.S. PATENT DOCUMENTS

| | | | |
|---|---|---|---|
| 2,579,251 | 12/1951 | Coates et al. | 260/448 AD |
| 2,666,076 | 1/1954 | Rex et al. | 260/448 AD |
| 2,687,423 | 8/1954 | Mesirow | 260/448 AD |
| 2,845,447 | 7/1958 | Carlson | 260/448 AD |
| 2,965,663 | 12/1960 | Smith et al. | 260/448 AD |
| 3,094,546 | 6/1963 | Towers | 260/448 AD |
| 3,717,666 | 2/1973 | Kobetz et al. | 260/448 AD |
| 3,845,447 | 7/1958 | Carlson et al. | 260/448 AD |

*Primary Examiner*—Helen M. S. Sneed

[57] ABSTRACT

Stable solutions of aluminum alkoxides are prepared by reacting aluminum metal with a mixture containing isobutyl alcohol and n-butyl alcohol in which the mole ratio of isobutyl alcohol to n-butyl alcohol is from 1:1 to 20:1.

4 Claims, No Drawings

STABLE ALUMINUM ALKOXIDE SOLUTIONS

This invention relates to stable solutions of aluminum butoxides and more particularly to a process for preparing stable solutions of aluminum butoxides having increased solubility in the reaction medium.

It is known that lower aluminum alkoxides solidify when stored for a period of time, i.e., they deteriorate upon exposure to moisture and air, even when stored in a sealed container, to form aluminum oxide and alcohol. It is desirable, however, to maintain the aluminum alkoxides of lower alkyl alcohols in their liquid form for extended periods of time so that they can be stored, shipped and used in their liquid form without the addition of solvents. Since these aluminum alkoxides have a variety of uses such as in the formation of catalysts and as additives for paints, it is desirable that these liquid aluminum alkoxides be stable over long periods of time.

Stable liquids blends of aluminum alkoxides have been prepared in accordance with U.S. Pat. No. 2,687,423 to Mesirow by mixing aluminum alkoxide which normally solidifies to the hard crystalline state, for example, ethyl, normal or isopropyl aluminum trialkoxide, aluminum n-butyl trialkoxide with a critical amount of aluminum trisecondary butoxide to form a mixed product which is stable for a considerable period to time. However, the resulting product does not contain the concentration of aluminum alkoxide which is desired, for example, in the preparation of catalysts.

Thus, applicants have found that stable solutions of aluminum alkoxides can be prepared from aluminum metal and a mixture of isobutyl alcohol and n-butyl alcohol and that these concentrated solutions have improved stability over longer periods of time when compared with the previously mentioned aluminum alkoxides.

Moreover, the solutions of aluminum butoxides produced in accordance with this invention contain a higher concentration of aluminum alkoxides than have been prepared heretofore. For example, stable solutions containing up to 90 percent by weight of aluminum butoxides have been prepared by the process of this invention.

Therefore, it is an object of this invention to prepare stable aluminum butoxide solutions. Another object of this invention is to prepare a stable solution of mixed aluminum butoxides. Another object of this invention is to prepare stable solutions containing increased concentrations of aluminum butoxides. Still another object of this invention is to prepare stable solutions in which the concentration of aluminum alkoxides in the solution is greater than 20 percent. A further object of this invention is to provide a process for preparing stable solutions of mixed aluminum butoxides.

The foregoing objects and others which will become apparent from the following description are accomplished in accordance with this invention, generally speaking, by providing a stable solution of mixed aluminum alkoxides. The solution of mixed aluminum alkoxides is prepared by reacting metallic aluminum with a mixture containing isobutyl alcohol and n-butyl alcohol in a mole ratio of 1:1 to 20:1.

Hereinafter aluminum alkoxides will, for purposes of convenience, be set forth and represented by the formula $Al(OR)_3$ wherein the OR group is an alkoxy group having 4 carbon atoms.

While applicants do not wish to be bound by theoretical considerations, the reaction of the respective reactants may be thought of as proceeding along the lines of the equation set forth below $$Al + 3ROH \rightarrow Al(OR)_3 + 1.5H_2$$

In the above equation, it will be noted that the reaction generally proceeds by the reaction of about 3 moles of the alcohol per gram atom of aluminum to produce the alkoxide along with the liberation of hydrogen gas. The R group of the aluminum alkoxide represents an alkyl radical having 4 carbon atoms which is derived from a mixture containing isobutyl and n-butyl alcohol.

We have found that by using a mixture of isobutyl alcohol and n-butyl alcohol that a solution can be obtained having a greater concentration of aluminum alkoxides than could have been prepared heretofore using a single alcohol.

In accordance with the process of this invention, the aluminum alkoxides are obtained by reacting aluminum metal with a mixture of isobutyl alcohol and n-butyl alcohol in the presence or absence of catalysts or promoters. One method of carrying out the invention is described in U.S. Pat. No. 2,845,447 to Carlston et al in which the aluminum metal and mixture of isomeric alcohols are introduced into a reaction zone maintained under sufficiently high pressure to maintain at least part of the mixture of isomeric alcohols therein in the liquid phase and at temperatures sufficiently high to assure interaction of the aluminum metal and the alcohols. The mixture of alcohols and aluminum is introduced into the reaction zone at such a controlled rate that only a portion of the total aluminum metal present at any one time in the reaction zone is immersed in the liquid phase. Thus, the process of this invention may be carried out in an elongated reaction zone which is filled to a substantial degree with pieces or fragments of aluminum metal. The mixture of isomeric alcohols is introduced into the lower part of the reaction zone which is under sufficient pressure to maintain at least a portion of the alcohol in the liquid phase. The reaction zone is maintained at an elevated temperature, thus assuring interaction between the aluminum metal and the alcohols to form aluminum alkoxides and hydrogen. The aluminum alkoxides and unreacted alcohols are withdrawn at a point intermediate between the lower part and the upper part of the reaction zone, while the mixture of isomeric alcohols is continuously introduced into the lower part of the reaction zone. Liquid is withdrawn therefrom at a controlled rate thus assuring a substantially continuous contact of alcohol with the lower part of the aluminum bed. The liquid level in the reaction zone is maintained at all times substantially below the upper level of the aluminum bed. Aluminum metal is continuously or intermittently introduced into the upper part of the reaction zone to maintain the upper level of the aluminum bed at a height substantially above that of the liquid level in the lower part of the reaction zone.

The aluminum alkoxides of this invention may also be prepared using the techniques described in U.S. Pat. Nos. 3,965,663 to Smith et al and 3,094,546 to Towers. In accordance with the process disclosed therein, the mixture of isomeric alcohols is added to a vaporizer attached to a column which is packed with particles of aluminum. At the top of the column is a combination condenser and vent which allows any gas such as hydrogen, formed during the reaction to be released from the apparatus. The mixture of alcohols are heated to reflux temperature and the alcoholic vapors rise upward through the column where a portion of the alcohols react with the aluminum packing in the column to form the aluminum alkoxides.

Uncondensed alcohols and hydrogen gas, which is formed as a reaction by-product, continue to rise through the packed column into the condenser where the alcohols are condensed and returned to the vaporizer through the column where they react with the particles of aluminum. When sufficiently concentrated, the aluminum alkoxide liquid is continuously withdrawn from the bottom of the vaporizer while a fresh alcohol mixture is added to the sytem.

Metallic aluminum employed in preparing the mixed aluminum alkoxides of this invention are in the form of pieces, fragments, chunks, pellets, turnings or the like. The average particle size of the particles may vary considerably. In general, it is preferred that the aluminum particles range in size from about 0.1 to about 3 inches and more preferably from about ⅛ to about 1 inch in diameter. Use of smaller or larger particles may be employed within the scope of this invention.

The process of this invention is carried out at a temperature range of, for example, from about 100° to about 120° C. at atmospheric pressure. The specific temperature employed will depend largely upon the pressure in the system and composition of the alcohol mixture. Although the temperature range is not critical, the temperatures should be maintained below those which will result in the decomposition of the resultant aluminum alkoxides. The aluminum alkoxides may be prepared by a batch, semi-continuous or continuous process and at subatmospheric, atmospheric or superatmospheric pressures. Pressures ranging from about atmospheric to about 500 psig and higher may suitably be employed. In general, it has been found that pressures of from 15 to about 100 psig and more preferably from 20 to 50 psig are particularly suitable.

It has been found that no catalyst or activator is required to initiate the reaction between the aluminum metal and mixture of alcohols. Once initiated, the reaction is of an exothermic nature. All that is required to continue the reaction after initiation is to continuously replace the alcohols and aluminum metal used up in converting the aluminum to aluminum alkoxides. This is easily attained by adding aluminum metal and the alcohols to the reaction mixture at a rate sufficient to maintain a constant reflux temperature.

Catalysts or activators may be employed to initiate the reaction, if desired. Examples of suitable catalysts or activators are alcoholic solutions of mercuric chloride, ferric chloride, stannic chloride, cupric chloride, boron trioxide or iodine. Other activators which may be employed are the alkoxy alcohols described in U.S. Pat. No. 3,717,666 to Kobetz. Residual aluminum from the process of this invention also acts as an activator.

The amount of activator is not critical and may range from about 0.1 to about 15 weight percent of the activating agent based on the weight of the aluminum. When the alkoxy alcohols are employed as activators, the amount of alkoxy alcohol is preferably from about 5 to about 15 percent by weight based on the weight by the aluminum.

When the aluminum is reacted under optimum conditions with the mixture of alcohols, i.e., about 30 mole percent n-butyl alcohol and 70 mole percent isobutyl alcohol, a stable aluminum alkoxide solution is obtained. Generally the product is used as a solution, however, the product may be further purified, if desired, by distilling off the unreacted alcohols from the aluminum alkoxides.

The aluminum alkoxides prepared in accordance with this invention may be employed in the preparation of catalysts or other materials where it is desirable to impregnate a support and thereafter hydrolyze the aluminum alkoxides to form active aluminum oxide catalysts. Also, with the increased concentration of the aluminum alkoxides in the solution, greater production rates are achieved in Oppenauer type oxidations.

The embodiments of this invention are further illustrated by the following examples. All parts are by weight unless otherwise specified.

A laboratory prototype of the reactor described in U.S. Pat. No. 3,094,546 to Towers was used in the following examples:

EXAMPLE 1

A column containing residual aluminum from a previous reaction was filled with 2S grade aluminum tubing ¼ × 1 inch and the vaporizer was filled to the working level with a mixture containing 118.4 parts of n-butyl alcohol and 29.6 parts of isobutyl alcohol. The system was heated to reflux temperature whereupon the vapors in the column reacted with the aluminum, generating hydrogen gas. After refluxing for 30 minutes, about 80 liters (STP) of hydrogen gas were generated which corresponds to the formation of about 1.8 pounds of aluminum butoxide. The reaction was then terminated and the contents of the vaporizer transferred to a storage vessel. After standing for 3 days at room temperature, the supernatant liquid in the storage vessel was analyzed and found to contain about 10 weight percent of aluminum butoxide.

EXAMPLES 2–9

The procedure described in Example 1 was repeated using various ratios of n-butyl alcohol to isobutyl alcohol. The ratio of isobutyl alcohol and n-butyl alcohol employed and the solubility of the resultant aluminum butoxides in the saturated solution at 20° C. are shown in the following Table.

TABLE

| Ex. No. | Mole Percent n-Butyl Alcohol | Mole Percent Isobutyl Alcohol | Weight Percent Aluminum Butoxides In Saturated Solution at 20° C. |
|---|---|---|---|
| 1 | 80 | 20 | 10 |
| 2 | 50 | 50 | 15 |
| 3 | 45 | 55 | 44 |
| 4 | 35 | 65 | 59 |
| 5 | 30 | 70 | 90 |
| 6 | 25 | 75 | 85 |
| 7 | 20 | 80 | 70 |
| 8 | 10 | 90 | 54 |
| 9 | 5 | 95 | 23 |

These examples show that as the mole percent of isobutyl alcohol in the mixture increases from about 50 up to about 90 mole percent, there is a substantial increase in the solubility of the aluminum butoxide.

Although specific examples of the invention have been described herein, it is not intended to limit the invention solely thereto, but to include all the variations and modifications falling within the scope of the appended claims.

What is claimed is:

1. An improved process for preparing stable solutions of aluminum butoxides by reacting metallic aluminum with butyl alcohol, the improvement which comprises reacting metallic aluminum with a mixture containing isobutyl alcohol and n-butyl alcohol at the reflux temperature of the alcohols but below the decomposition temperature of the aluminum butoxides, said alcohols are present in a mol ratio of isobutyl alcohol to n-butyl alcohol of from 1:1 to 20:1.

2. The improved process of claim 1 wherein the metallic aluminum is contacted with the mixture of alcohols in the vapor phase to produce aluminum butoxides.

3. The improved process of claim 2 wherein the metallic aluminum is packed in a column.

4. A stable alcohol solution containing from 30 to 90 weight percent of aluminum butoxides which is obtained from the reaction of isobutyl alcohol and n-butyl alcohol in a mol ratio of from 1:1 to 20:1 with metallic aluminum.

* * * * *